US009579018B2

(12) United States Patent
Cornsweet et al.

(10) Patent No.: US 9,579,018 B2
(45) Date of Patent: *Feb. 28, 2017

(54) OCULAR FUNDUS CAMERA SYSTEM AND METHODOLOGY

(71) Applicant: Brien Holden Vision Diagnostics, Inc., Prescott, AZ (US)

(72) Inventors: Tom N. Cornsweet, Prescott, AZ (US); Paul R. Peterson, Prescott, AZ (US)

(73) Assignee: Brien Holden Vision Diagnostics, Inc., Ontario, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/974,947

(22) Filed: Dec. 18, 2015

(65) Prior Publication Data

US 2016/0100757 A1 Apr. 14, 2016

Related U.S. Application Data

(63) Continuation of application No. 13/409,056, filed on Feb. 29, 2012, now Pat. No. 9,247,876.

(60) Provisional application No. 61/448,342, filed on Mar. 2, 2011.

(51) Int. Cl.
| | |
|---|---|
| *A61B 3/14* | (2006.01) |
| *A61B 3/00* | (2006.01) |
| *A61B 3/10* | (2006.01) |
| *A61B 3/12* | (2006.01) |
| *G02B 27/00* | (2006.01) |
| *G02B 7/09* | (2006.01) |

(52) U.S. Cl.
CPC .............. *A61B 3/12* (2013.01); *A61B 3/0025* (2013.01); *A61B 3/14* (2013.01); *G02B 27/0068* (2013.01); *G02B 7/09* (2013.01)

(58) Field of Classification Search
CPC .......... A61B 3/103; A61B 3/14; A61B 3/152; A61B 3/113; A61B 3/1225; A61B 3/1015
USPC ........ 351/206, 208, 205, 210, 221, 246, 211
See application file for complete search history.

(56) References Cited

U.S. PATENT DOCUMENTS

| | | | |
|---|---|---|---|
| 3,536,383 A | 10/1970 | Cornsweet et al. | |
| 3,582,775 A | 6/1971 | Cornsweet | |
| 3,614,214 A | 10/1971 | Cornsweet | |

(Continued)

FOREIGN PATENT DOCUMENTS

| | | |
|---|---|---|
| CN | 101365932 A | 2/2009 |
| CN | 101495906 A | 7/2009 |

(Continued)

*Primary Examiner* — Dawayne A Pinkney
(74) *Attorney, Agent, or Firm* — Jones Day

(57) ABSTRACT

An ocular fundus camera system and an associated methodology. The system includes (a) an image sensor disposed along a fundus-image reflection path adjacent that path's downstream end, and in optical communication with light carried in this path, (b) an aperture centered on the reflection path's long axis, operatively associated with, and stationary with respect to, the sensor at a location which is upstream from the sensor, and (c), for accomplishing (1) precision fundus-image focusing on the sensor, and additionally (2) autorefraction, optical, light-content shifting structure, operable selectively for producing, within that portion of the reflection path which is disposed downstream from the shifting structure, relative trans-axial displacement solely of any non-collimated light carried in that portion of the main path which is disposed upstream from the shifting structure.

15 Claims, 3 Drawing Sheets

(56) References Cited

U.S. PATENT DOCUMENTS

Figure 1:
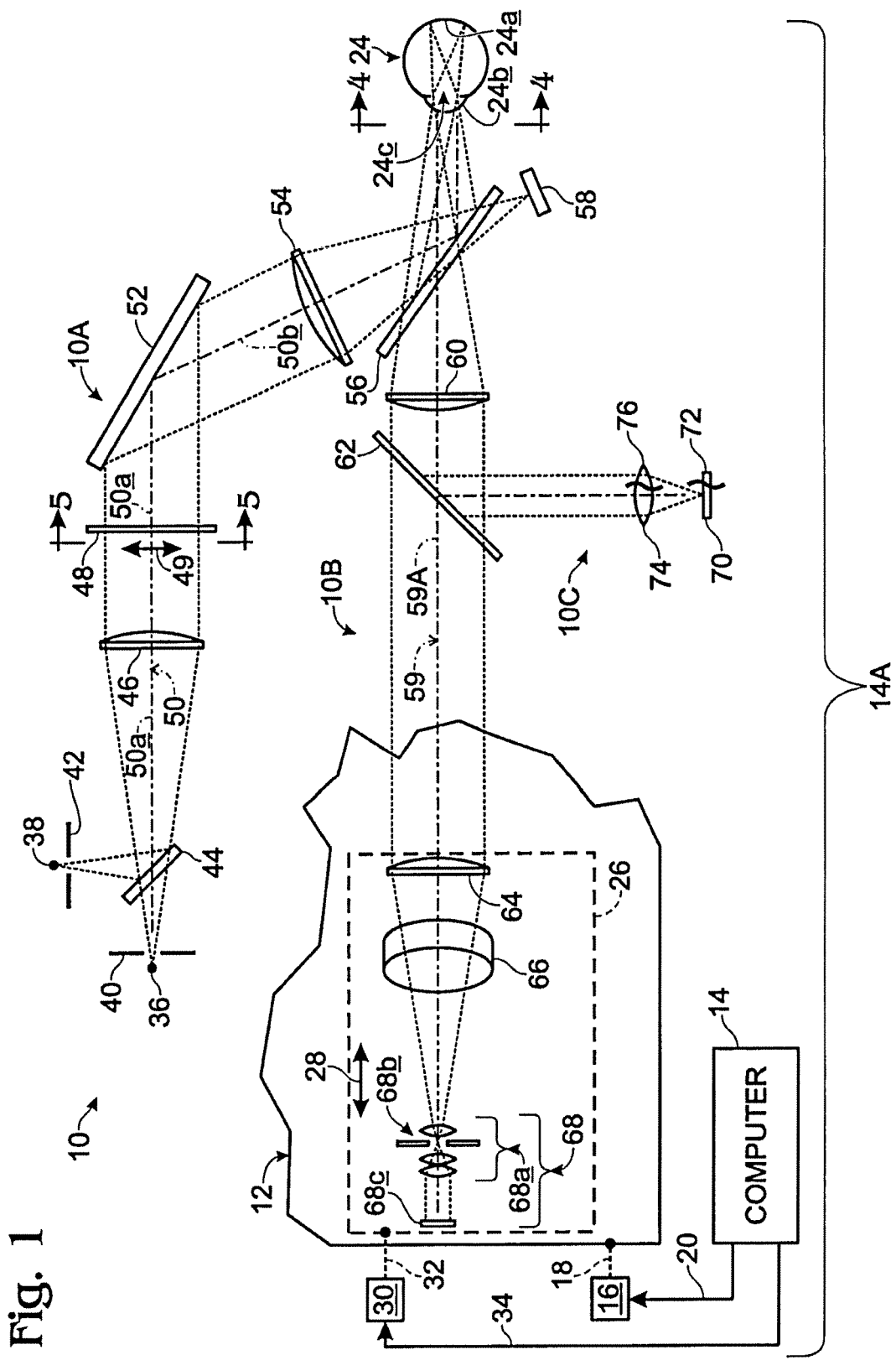

| | | |
|---|---|---|
| 3,639,041 A | 2/1972 | Cornsweet |
| 3,693,019 A | 9/1972 | Grenda et al. |
| 3,712,716 A | 1/1973 | Cornsweet et al. |
| 3,723,648 A | 3/1973 | Cornsweet |
| 3,724,932 A | 4/1973 | Cornsweet et al. |
| 3,804,496 A | 4/1974 | Cornsweet et al. |
| 3,819,256 A | 6/1974 | Bellows et al. |
| 3,832,066 A | 8/1974 | Cornsweet |
| 3,843,240 A | 10/1974 | Cornsweet |
| 3,864,030 A | 2/1975 | Cornsweet |
| 3,870,415 A | 3/1975 | Cornsweet |
| 3,963,019 A | 6/1976 | Quandt |
| 4,018,514 A | 4/1977 | Plummer |
| 4,019,813 A | 4/1977 | Cornsweet et al. |
| 4,281,926 A | 8/1981 | Cornsweet |
| 4,329,049 A | 5/1982 | Rigg et al. |
| 4,715,703 A | 12/1987 | Cornsweet et al. |
| 4,819,752 A | 4/1989 | Zelin |
| 5,042,937 A | 8/1991 | Cornsweet |
| 5,114,222 A | 5/1992 | Cornsweet |
| 5,196,872 A | 3/1993 | Beesmer et al. |
| 5,202,708 A | 4/1993 | Sasaki et al. |
| 5,210,554 A | 5/1993 | Cornsweet et al. |
| 5,410,376 A | 4/1995 | Cornsweet et al. |
| 5,422,690 A | 6/1995 | Rothberg et al. |
| 5,535,743 A | 7/1996 | Backhaus et al. |
| 5,560,356 A | 10/1996 | Peyman |
| 5,745,163 A | 4/1998 | Nakamura et al. |
| 5,820,557 A | 10/1998 | Hattori et al. |
| 5,886,780 A | 3/1999 | Fukuma et al. |
| 5,961,449 A | 10/1999 | Toida et al. |
| 5,969,815 A | 10/1999 | Toida et al. |
| 6,082,858 A | 7/2000 | Grace et al. |
| 6,152,875 A | 11/2000 | Hakamata |
| 6,296,358 B1 | 10/2001 | Cornsweet et al. |
| 6,325,512 B1 | 12/2001 | Wei et al. |
| 6,424,850 B1 | 7/2002 | Lambert et al. |
| 6,659,613 B2 | 12/2003 | Applegate et al. |
| 6,704,588 B2 | 3/2004 | Ansari et al. |
| 6,789,900 B2 | 9/2004 | Van de Velde |
| 6,830,336 B2 | 12/2004 | Fransen |
| 6,834,958 B2 | 12/2004 | Cornsweet et al. |
| 6,836,337 B2 | 12/2004 | Cornsweet |
| 6,885,882 B2 | 4/2005 | Cote et al. |
| 7,025,459 B2 | 4/2006 | Cornsweet et al. |
| 7,077,521 B2 | 7/2006 | Thomas |
| 7,118,217 B2 | 10/2006 | Kardon et al. |
| 7,156,518 B2 | 1/2007 | Cornsweet et al. |
| 7,167,736 B2 | 1/2007 | Winther |
| 7,360,895 B2 | 4/2008 | Cornsweet et al. |
| 7,470,025 B2 | 12/2008 | Iwanaga |
| 7,896,496 B2 | 3/2011 | Hammer et al. |
| 7,896,498 B2 | 3/2011 | Munger et al. |
| 2002/0063849 A1 | 5/2002 | Takeuchi et al. |
| 2004/0046935 A1 | 3/2004 | Copland |
| 2004/0138539 A1 | 7/2004 | Jay et al. |
| 2004/0489937 | 9/2004 | Okinishi |
| 2004/0263784 A1 | 12/2004 | Cornsweet et al. |
| 2005/0070772 A1 | 3/2005 | Cornsweet |
| 2005/0124869 A1 | 6/2005 | Hefti et al. |
| 2005/0143662 A1 | 6/2005 | Marchitto et al. |
| 2005/0157261 A1 | 7/2005 | Hanebuchi et al. |
| 2005/0171413 A1 | 8/2005 | Blair |
| 2005/0187443 A1 | 8/2005 | Routt et al. |
| 2006/0184040 A1 | 8/2006 | Keller et al. |
| 2007/0091265 A1 | 4/2007 | Kardon et al. |
| 2007/0146535 A1 | 6/2007 | Nanjo |
| 2007/0171366 A1 | 7/2007 | Su et al. |
| 2008/0231803 A1 | 9/2008 | Feldon et al. |
| 2008/0249381 A1 | 10/2008 | Muller et al. |
| 2009/0059169 A1 | 3/2009 | Shimizu et al. |
| 2009/0116214 A1 | 5/2009 | Phillips, III et al. |
| 2009/0201490 A1 | 8/2009 | Gerlitz |
| 2010/0110379 A1 | 5/2010 | Zhou et al. |
| 2010/0152558 A1 | 6/2010 | Gerlitz |
| 2010/0201944 A1 | 8/2010 | Lewis et al. |
| 2010/0277692 A1 | 11/2010 | Mukai et al. |
| 2011/0105858 A1 | 5/2011 | Cho et al. |
| 2011/0184261 A1 | 7/2011 | Menon |

FOREIGN PATENT DOCUMENTS

| | | |
|---|---|---|
| EP | 1452126 | 1/2004 |
| JP | 2004-267616 A | 9/2004 |

OCULAR FUNDUS CAMERA SYSTEM AND METHODOLOGY

CROSS REFERENCE TO RELATED APPLICATION

This application is a continuation of U.S. application Ser. No. 13/409,056, filed Feb. 29, 2012, and claims the benefit of U.S. Provisional Application No. 61/448,342, filed Mar. 2, 2011. Both of these applications, in their entirety, are incorporated herein by reference.

BACKGROUND AND SUMMARY OF THE INVENTION

This invention pertains to an ocular fundus camera system and methodology. Hereinafter in the discussion of this field, and in the description presented regarding the present invention, the single term "fundus" will be used in most instances, with the understanding that all such references relate to the ocular fundus.

The inside back surface of the eye, which contains the retina, the blood vessels, and the neural tissue, is called the ocular fundus. Many systemic pathologies, as well as ocular ones, cause changes in the appearance of the fundus, and as a consequence, virtually all ophthalmic exams, and most general physical exams, include observations of the fundus. Such observations are most often performed using a device called an ophthalmoscope, a hand-held device that provides the observer with a magnified direct view of the fundus through a subject's pupil.

Unfortunately, there are many factors that limit the usefulness of ophthalmoscope examinations. Among the major ones of these limitations are (a) that most ophthalmoscopes have rather poor optical resolution—a factor considerably limiting the fundus detail which is visible, (b) that continuous eye movement makes observation very challenging, (c) that the opportunity for clarity-enhancing image magnification is minimal, and (d), that, in the use of an ophthalmoscopic device, no permanent record of an examination is created.

To overcome these difficulties, in a mode aimed essentially at functional replacement of the use of ophthalmoscopic devices, certain prior art camera systems and associated methodologies have been developed which operate in various ways to capture, hopefully in the best way possible, detailed images of the fundus—thus to enable more precise and confident examination of the various conditions which may be detected through observing a clear image of the fundus.

The present invention focuses attention generally in this same area of ocular-fundus camera systemic and methodologic development, but does so in a manner which turns out to offer an improved and very high degree of extremely well-focused image accuracy, and in a system and methodologic approach which is relatively simple, and which can be systemically constructed, and methodologically used with camera equipment, and related optical and electronic (including digital computer) components, which are, for various reasons, considerably less costly, and ultimately more accurate in terms of fundus-image clarity, than what have been employed in prior-art.

The invention especially offers, in this setting, significant improvements in the visual (and other) presentation quality of fundus-based information usable in assessing the various kinds of matters regarding which accurate detection of fundus condition is so important. Further, the invention additionally offers a distinctly new way to perform accurate autorefraction.

As will be seen, an important feature of the invention which is highly relevant to both its structural and its operational advantages, is the included presence, systemically, of what is referred to as a light-shifting structure, or optical, light-content shifting structure—a structure which, among other things, (a) greatly simplifies and reduces equipment costs, (b) enhances focusing clarity and accuracy of an obtained fundus image, (c) readily enables the obtaining and presentation of stereo fundus images, and (d) is central to the just-above-mentioned autorefraction capability of the invention.

Accordingly, from one structural point of view, the invention proposes an ocular fundus camera system usable in relation to a light-illuminated fundus in a subject's eye, and including an elongate, main optical path which, in an operative condition of the system, extends downstream from the eye and carries fundus-reflection light derived from, and possessing a reflection image of, the fundus, this system including (a) an image-detecting sensor disposed along the main path at a location which is downstream from the eye in optical communication with fundus-reflection light carried in this path, and (b) structure operatively associated with the sensor, upstream from the eye, for introducing, into light reflected from the fundus, edge-portion-containing optical contrast imagery having at least one, contrast edge portion whose spatial disposition in the fundus-reflection light is independent of eye movement.

From another structural perspective, the invention features an ocular fundus camera system which, in an operative condition, includes (a) light-source structure for illuminating, along an elongate, illumination path, the fundus in a subject's eye, (b) an elongate, main optical path having upstream and downstream ends and a long axis, extending downstream from the subject's eye, and carrying, downstream along its length, both light that acts as if the pupil were its source, and light reflected from, and carrying an image of, the fundus (referred to also herein as fundus reflection light), (c) an image-detecting sensor centered on the main path's long axis adjacent the latter's downstream end, disposed for optical communication with light carried in the main path, (d) an aperture also centered on the main path's long axis, operatively associated with, and stationary with respect to, the sensor at a location which is upstream along the main path from the sensor, positioned there to communicate to the sensor light carried in the main path, (e) discriminatory, light-content shifting structure disposed centrally on the main path's long axis upstream therealong relative to the aperture, operable selectively for producing, within that portion of the main path which is disposed intermediate the shifting structure and the aperture, relative trans-axial displacement-shifting solely of any non-collimated light carried in that portion of the main path which is disposed immediately upstream from the shifting structure, and (f) structure selectively placeable across the illumination path for introducing, effectively, into light reflected from the fundus, edge-containing optical contrast imagery having at least one, contrast edge portion which lies at an angle relative to the direction of trans-axial shifting producible by the shifting structure, and whose spatial disposition in the fundus-reflection light is independent of eye movement.

From still a further structural point of view, what the present invention proposes is an ocular fundus camera system usable in relation to a light-illuminated fundus in a subject's eye, including, as cooperative, systemic elements, (a) an image-detecting sensor (preferably electronic) disposed centrally along, and adjacent the downstream end of, a main optical path which extends downstream from a subject's eye for receiving an image reflected from the illuminated fundus, (b) a fundus-image-passing (to the sensor) aperture centered on the main path's long axis at a location which is upstream from, and, significantly, stationary relative to, the sensor, and (c) disposed appropriately upstream from the aperture, discriminatory, light-content shifting structure, operable selectively for producing, within that portion of the main optical path which extends immediately downstream from the shifting structure, relative trans-axial displacement solely of any non-collimated light carried in that portion of the main optical path which is disposed just upstream from the shifting structure.

The concept of discriminatory, relative trans-axial light-flow (light-content) displacement refers to the ability of the light-shifting structure to discriminate, "in a shifting sense", between collimated and non-collimated light.

The system of the invention, in still a more specific manner of thinking about it additionally includes an appropriately (conventionally) algorithmically programmed digital computer which is operatively connected to selected system elements, including the sensor from which it is adapted to receive sensor-detected imagery. By inclusion of this thus-involved computer, any relative trans-axial displacement produced by the light-shifting structure, which displacement is then detected by the sensor, and through the sensor also by the connected computer, causes the computer to respond to detected light-shifting in a manner designed, under precision computer control, to minimize, via certain systemic optical adjustments, the presence of non-collimated fundus reflection light carried in that portion of the main optical path which is disposed upstream from the shifting structure. Such minimizing activity functions accurately to achieve dramatically clear focus of a fundus image on the sensor. The amount and direction of detected light shifting furnishes the necessary, relevant, fundus-image focus-correcting information to the computer.

In the preferred and best-mode embodiment of, and manner of practicing, the invention, the light-shifting structure takes the form of what we call a parallel plane shifter—a flat (i.e., having a plane), parallel-flat-opposite-sided piece of optically clear glass, herein having a chosen thickness of about 12.5-mm, and a circular, perimetral outline with a diameter of about 1-inches. Other sizes and shapes may be chosen for use, if desired depending upon other, freely user chooseable, system design features. This parallel plane shifter is also referred to herein as a discriminatory, light-content shifting structure, as an optical, light-content shifting structure, and as a device which is operable to produce a certain character of relative, trans-axial, light-flow displacement which will be explained later herein.

There are other interesting, and to some extent tangential, structural aspects of, and structural, collateral considerations associated with, the system of the invention as just generally discussed above, such as a few which involve, essentially, optical-element positioning and tracking, both manual (where appropriate), and under computer control, relative to the eye. Many of these other matters concern conventional practices that are not central to the system-internal optical features which are newly offered by the invention, and accordingly, while mentioned at appropriate points in the detailed description of the invention, are not specifically elements of the invention. These other matters, therefore, beyond the making of simple references to them, and recognized to be implementable in a variety of different ways, are left, for systemic implementation, appropriately "in the hands" of those generally skilled in the relevant art who are very knowledgeable about them.

From one operational point of view, the invention proposes an ocular fundus-imaging camera methodology usable, in relation to a light-illuminated fundus in a subject's eye, to apply to an image sensor a precision-focused image of the fundus contained in an elongate flow of reflection light coming from the fundus, this methodology including the steps of (a) discriminatorily, effecting trans-axial light-flow shifting, in a defined portion of the reflection flow, and relative to the long axis of that flow, solely of non-collimated light present in that defined portion, and (b) achieving fundus image focus by performing an operation which prevents any such shifting with respect to the reflection-carried fundus image content, per se.

From another operational perspective, the invention sets forth an image-forming, ocular fundus camera methodology including (a) placing, by external illumination, and projection onto the fundus, a contrast image possessing a contrast edge whose spatial position is independent of eye movement, (b) by such placing, creating, in a main, external optical path, a reflection-flow from the fundus which contains an image of the contrast edge which, depending upon the existence or absence of correct fundus focus, will be contained, respectively, in either collimated or non-collimated light, and (c) achieving proper fundus focus by making an adjustment to assure that, within the main optical path, the contrast-edge image content carried therein is present in collimated light.

From still a further operational viewpoint, and in relation to the invention's autorefraction capability, the present invention presents an ocular fundus camera methodology including the steps of (a) illuminating the fundus in a subject's eye along a main optical path having a long axis, (b) by such illuminating, creating a light reflection from the fundus which flows therefrom outwardly through the pupil in a flow of reflection light which is directed downstream from the eye along the main optical path's long axis, (c) discriminatorily, and in a relative trans-axial displacement manner at a location along the main optical path which is disposed downstream from the eye, shifting solely any non-collimated light which is contained in the flow of created reflection light, (d) detecting any such shifting, and (e) employing any detected shifting in a manner designed to aid in performing autorefraction.

Practice of the invention additionally features an ocular fundus, image-focusing—camera methodology expressible as including (a) illuminating the fundus in a subject's eye along an elongate illumination path, (b) by such illuminating, creating a light reflection from the fundus directed therefrom outwardly through the pupil in a flow of reflection light which progresses downstream from the eye along an elongate main optical path having a long axis, (c) discriminatorily, and in a relative trans-axial displacement manner at a location along the main optical path which is disposed downstream from the eye, shifting solely any non-collimated light which is contained in the flow of created reflection light, (d) detecting any such shifting, and (e) employing any detected shifting in a manner designed to minimize the presence of non-collimated light in the reflection-light flow.

Commenting on the invention methodology with a bit more specificity, the mentioned shifting is preferably performed by selected rotation, on the long axis of the mentioned main optical path, of a rotatable parallel plane shifter there placed in a condition with its plane disposed at a modest (such as about 9-degrees) angle relative to a plane disposed normal to the main optical path's long axis.

Even more specifically, the invention methodology further includes, in a manner non-movably centered on the main optical path's long axis, and at another location along that axis (than where the mentioned parallel plane shifter is disposed), which other location is located downstream from the shifter location, aperturing a portion of the flow of reflection light, and, downstream from where aperturing takes place, and at the location wherein the mentioned detecting occurs, performing such detecting by electronically sensing the apertured light-flow portion, with the step featuring minimization of non-collimated light presence in the reflection light flow involving using an outcome (by way of computer action) of the performing of electronic sensing. The verbal term "aperturing" is introduced and employed herein to mean the act of directing a light flow through a defined optical aperture, as in a camera.

Non-movability, relative to the main optical path's long axis, of that which performs aperturing, according to the invention, combined with the discriminatory light-shifting behavior, and use, of a parallel plane shifter, are significant invention features—fundus-imaging advances—which allow, among other things, for the use of inexpensive, electronic (digital) camera equipment for optical image sensing and image presentation.

As explained generally above, the minimizing of non-collimated light presence in the reflection light flow effects focusing of the apertured light flow at the location where sensing occurs so as to obtain a well-focused image of the illuminated fundus.

Other methodologic features of the invention, of course, exist, and these other such features, along with the above-mentioned, and other, systemic structural features of the invention, will become more fully apparent as the detailed description of the invention presented below is read in conjunction with the accompanying drawings.

DESCRIPTIONS OF THE DRAWINGS

FIG. 1 is a fragmentary, block/schematic diagram, in side-elevational-view form, of an ocular fundus camera system constructed in accordance with a preferred and best-mode embodiment of the invention, designed to practice the associated methodology of the invention, and illustrated in proper position relative to a subject's eye which is drawn schematically adjacent the right side of this figure. Components, relative positions between them, the schematically illustrated human eye, and various angles presented in this drawing figure, are not necessarily drawn to scale.

Figure 2:
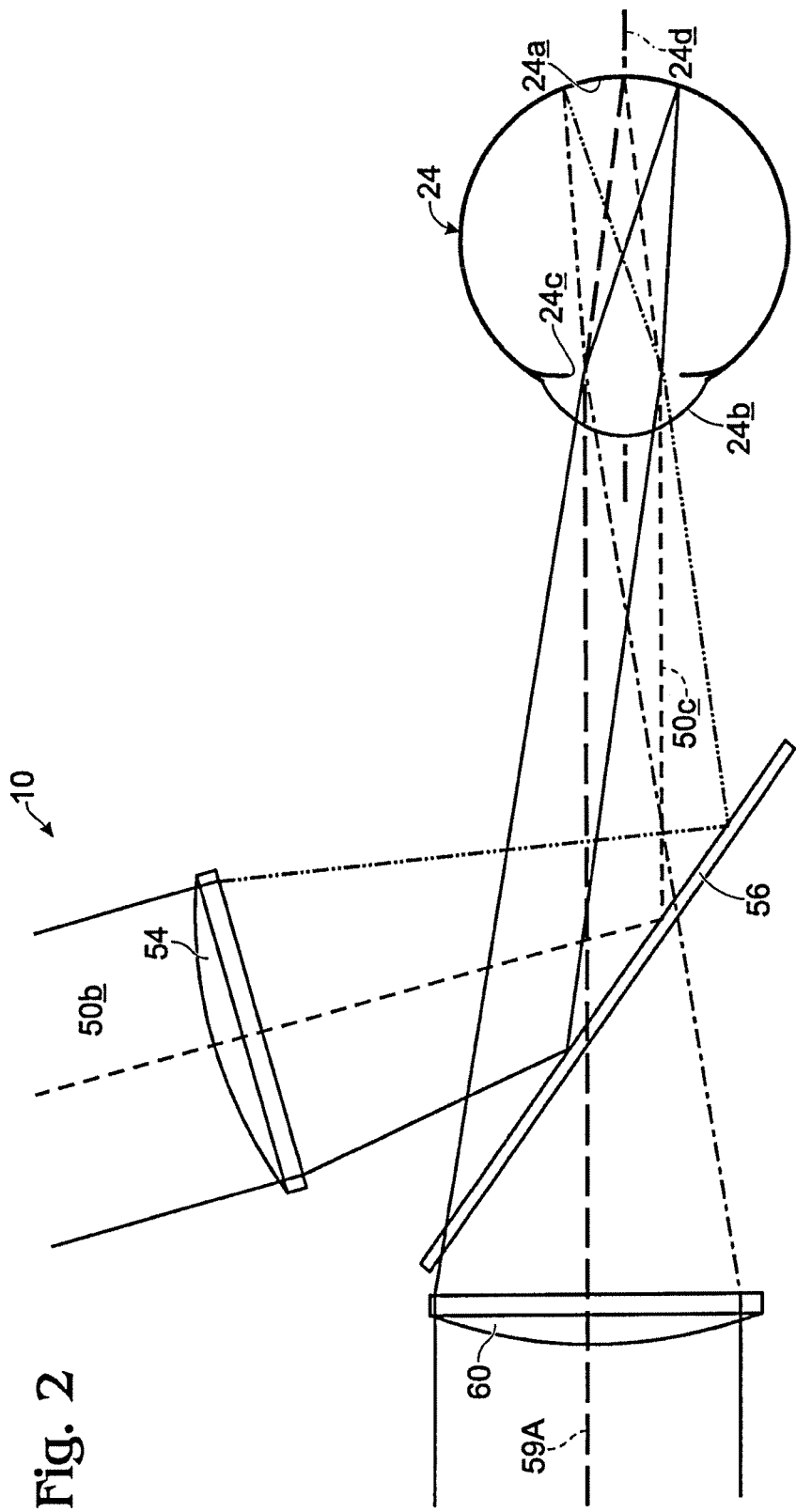

FIG. 2 is an enlarged detail of a portion of the system shown adjacent the right side in FIG. 1, focusing on the area therein which includes both the illustrated eye, and certain, optical, light-flow lines that are shown extending within, and disposed outwardly immediately adjacent the left side of, the eye in this figure. Differentiated, respective line characters are employed regarding these light-flow lines in order to clarify how they individually "pass" and continue between the inside and the outside of the eye.

Figure 3:
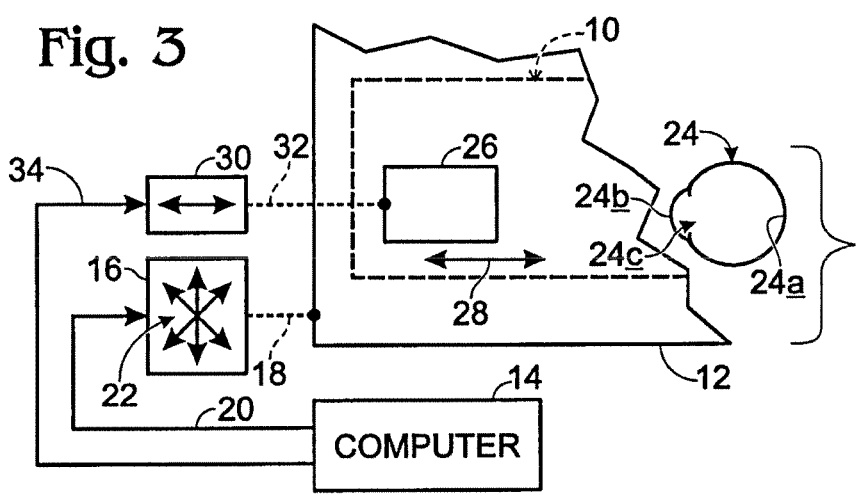

FIG. 3 is a simplified, fragmentary, block/schematic diagram illustrating certain motion-permitted structures that are included in the system of FIG. 1, movable in different specific manners under the control of an operatively connected digital computer to assist both in the positioning of all system elements properly relative to a subject's eye, and additionally, to achieve correct focus of a fundus image which is to be projected in the system onto an electronic optical sensor, or electronic device, such as a CCD sensor in a conventional electronic digital camera.

Figure 4:
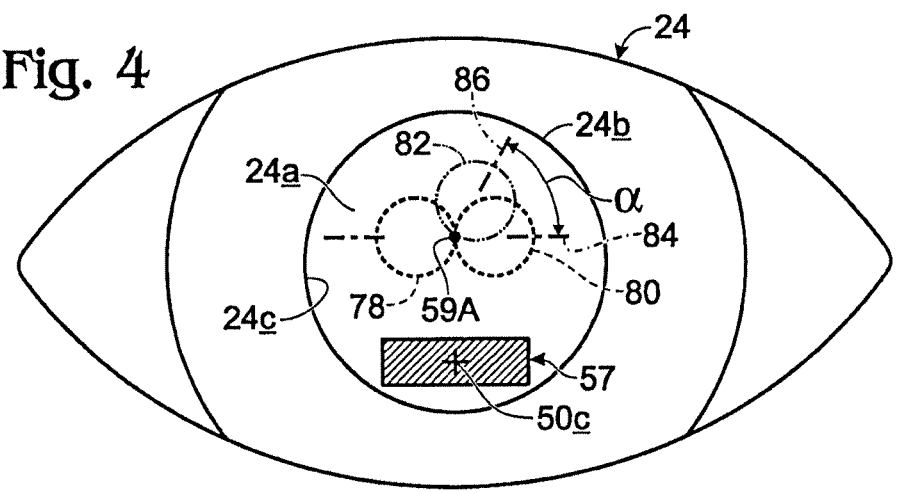

FIG. 4 is an enlarged, simplified, stylized and schematic illustration, presented from the point of view of the front of an eye, taken generally along the line 4-4 in FIG. 1, and showing both an eye-light-input aspect of fundus-illumination, and several conditions involving illumination-created fundus-image-reflections, that characterize different, specific fundus-imaging operations of the system of FIG. 1—operations that occur both during fundus-image focusing, and during autorefraction, procedures.

Figure 5:
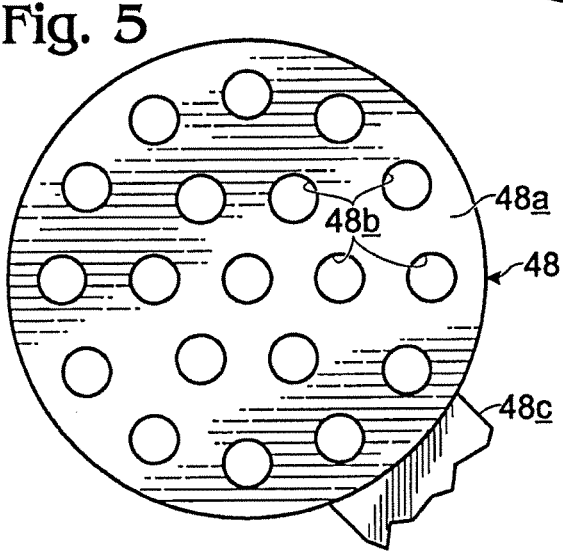

FIG. 5 is a fragmentary view, drawn on a larger scale than that which is employed in FIG. 1, illustrating a patterned reticle which is employed in accordance with certain practices of the present invention to create, under certain circumstances, a useful contrast-image pattern as a projection on a subject's fundus designed to aid, among other things, in precise fundus-image focusing.

DETAILED DESCRIPTION OF THE INVENTION

Beginning with FIGS. 1-3, inclusive, in the drawings, indicated generally at 10 is an ocular fundus camera system constructed in accordance with a preferred and best-mode embodiment of the present invention. In FIG. 3, system 10 is represented fragmentarily in dashed lines.

As will be more fully explained shortly, system 10 includes a number of interactive optical elements, or components, nearly all of which, as individuals, are entirely conventional both in construction and in operational features. These components, we appreciate, may be incorporated, properly collaboratively combined, in modified embodiments of the system of the invention, with these components possessing a wide variety of recognized, readily user-chooseable, and fully satisfactory, optical characteristics that are not individually critical to successful implementation of the invention. Accordingly, details of these several elements, except to the extent believed necessary to convey a clear understanding of how system 10 performs, will not be discussed. Rather, we will rely appropriately on the knowledge and skill of those generally skilled in the art of optics, and on the below-described, fully-informative operational description of system 10, as being entirely adequate to enable those skilled in the art to build and use the illustrated system. In this context, and reinforcing what we have just said immediately above, we appreciate that specific sizes and particular optical characteristics of various ones of the illustrated elements herein may lie within ranges of completely usable characteristics, and we completely appreciate that such characteristics, and appropriate ranges thereof, will be well within the knowledge and skill of people skilled in the art.

In the embodiment of the invention illustrated in the drawings and now being described, all of the system-included optical elements, referred to as the optical-component content of system 10, are appropriately mounted/supported upon a multi-axially positionally movable/adjustable main frame 12 which, under the controlling influence of an appropriately algorithmically programmed digital computer 14, may be positionally and reversibly shifted and adjusted, translationally and rotationally as required, on and about any one or more of the three, conventional orthogonal axes, by operation of appropriate stepper-motor structure 16 (which may include several motors), of suitable, conventional design—this motor structure being suitably and conventionally drivingly connected to frame 12, as indicated by a dashed line 18. The relevant, operative, control connection which exists between computer 14 and motor structure 16 is represented by a single-arrow-headed line 20. The three, recognized orthogonal axes just mentioned are represented generally at 22 in the block in FIG. 3 which represents motor structure 16. Frame 12 is suitably supported conventionally to permit the described spatial, positional adjustments of the supported system-10 components As will be more fully explained later, operation of motor structure 16 to adjust the spatial position of frame 12 and what it carries, is done for the purpose of initially correctly positioning all of the optical elements in system 10, as a systemic unit, relative to a subject's eye whose fundus is to be examined, such as the fundus 24a in the eye which is pictured at 24 in FIGS. 1-3, inclusive. The cornea in eye 24 is indicated at 24b, and its pupil at 24c. The vertical centerline (horizontally drawn) of eye 24 is shown at 24d in FIG. 2. In these three drawing figures, system 10 is shown in a correctly positioned operative condition relative to eye 24.

As will also be more fully explained later, certain ones of the optical elements that make up a portion of the optical-component content of system 10, and which elements are relevant to the functional action—a motion action—of focusing a fundus image properly on an optical sensor which is included in the system, are specifically mounted on a subframe 26 (seen in dashed lines in FIG. 1, and in solid lines in FIG. 3) which is appropriately carried on frame 12 for relative, reversible translation on this frame generally as indicated by a double-headed arrow 28 in FIGS. 1 and 3. Such translational motion of subframe 26 which, along with its several, mounted optical components, are collectively referred to herein as a focusing assembly 26, takes place under the driving influence of an appropriate, conventional stepper-motor structure 30 which is drivingly connected through drive connection, pictured by a dashed line 32, established between it and subframe 26. Operation of motor structure 30 is controlled through an operative control connection represented by an arrow-headed line 34 extending between it and computer 14.

With attention now directed especially to FIG. 1, system 10, in general terms, may be viewed as possessing three optical branches, including a fundus-illumination branch 10A, a main, reflection-flow branch 10B, and a system initial-positioning branch 10C. System components included in branch 10A are responsible for illuminating a fundus which is to be examined. Branch 10B is responsible for receiving light reflected from an illuminated fundus, and for precisely focusing and directing this light for imaging of a fundus on an image sensor. Branch 10C is responsible, at the beginning of an eye-fundus examination, to ensure proper positioning of the entirety of the optical content in system 10 relative to an eye whose fundus is to be examined.

With regard to certain components (light sources, a particular pair of motor structures, and image sensors in digital cameras) that are included in these branches, and in order not further to overcrowd FIG. 1 with drawing lines, a simple bracket 14A is included in this figure to represent a number of the relevant, operative control and data-collection connections which exist between these components and computer 14. These so-represented connections, not individually illustrated, will be described later herein.

Included in fundus-illumination branch 10A, optically sequentially in a downstream progress sense, and beginning from its upstream end, are two, elongate, LED light sources 36, 38, represented as large dots in FIG. 1, and collectively referred to as light-source structure, a pair of centrally-elongate-slit-furnished aperture plates 40, 42, each with an elongate, central, rectangular, slit aperture, associated with light sources 36, 38, respectively, a dichroic mirror 44, a circular-perimeter doublet lens 46, a position-adjustable, shadow-patterning reticle 48, also referred to herein as structure for introducing, into light reflected from the fundus (called fundus-reflection light which carries a reflection image of the fundus), what we refer to as edge-portion-containing contrast imagery having at least one contrast edge portion, which reticle can be swung into and out of the elongate, optical illumination path (or simply illumination path) 50 which is associated with system branch 10A, a mirror 52, another circular-perimeter doublet lens 54 which has the same size and optical design as lens 46, a beam splitter 56, and a light trap 58.

Adding now attention reference to FIG. 2 along with FIG. 1, as can be seen, illumination path 50, which is optically centrally associated with illumination branch 10A, is what may be called plural-angular in nature, in the sense that, with respect to the furnishing of fundus illumination, it includes three, principal, angular portions which, progressing downstream along path 50, are designated, sequentially, 50a, 50b, 50c. The lines in FIG. 1 which represent path portions 50a, 50b, 50c also represent the respective long, optical axes of these path portions. To be noted particularly regarding these three path portions as they are drawn in FIGS. 1 and 2, is that path portion 50a is horizontal, that path portion 50b is inclined steeply downwardly and to the right in the figures (relative to path portion 50a), and, importantly, that path portion 50c is also horizontal, and specifically disposed so that it extends toward the lower part of pupil 24c in eye 24. This "low-in-the pupil" eye-engagement condition for path portion 50c plays a special role regarding how fundus illumination light enters the eye. Especially important to observe, in relation to this just-mentioned fundus-illumination, "enters the eye" statement, is that path portion 50c does not coincide with, and is in fact intentionally positioned below, the shortly to be described central optical axis associated with reflection-flow branch 10B.

Each of light sources 36, 38 has a three-die-linearly-assembled, elongate configuration, and specifically such a configuration which has a length, measured essentially normal to the plane of FIG. 1, of about 3-mm, and a width, measured essentially in the plane of FIG. 1 of about one 1-mm. In such a setting, each LED die in each light source has a square perimetral outline with lateral side dimensions of about 1-mm. The smaller (width) dimension of light source 36 extends essentially "vertically" in FIG. 1, and the smaller (width) dimension of light source 38 extends essentially "horizontally" in the plane of this figure. Each of these sources, when energized/operated, creates, and projects from it, an elongate 1×3-mm "ribbon" of light.

Light source 36 is an infrared, or simply a red, source operating at a wavelength of about 850(plus or, minus about 30)-nm, and light source 36 is a green source operating at a wavelength of about 540(plus or minus about 30)-nm. These two light sources are independently, and at different times, energized and operated, as will be explained later, under the control of computer 14, and accordingly, respective, appropriate, operative control connections, represented by previously described bracket 14A, extend between these two sources and the computer.

The elongate, rectangular, central slit apertures, or slits, which are provided in aperture plates 40, 42 with respect to light sources 36, 38, respectively, are spaced preferably drily a fraction of a millimeter away from their respective, associated light sources, and are (a) disposed with their long axes essentially paralleling the long axes of the plural-die-assembled light sources themselves, and effectively (b) "aligned" with the light sources so that with the light sources viewed through their respectively associated slit apertures, these apertures essentially fully expose the light sources "behind" them.

As is clearly illustrated in FIG. 1, light sources 36, 38 project orthogonally, i.e., along respective, orthogonally disposed axes (not labeled) toward opposite sides of dichroic mirror 44 which is constructed, optically, to pass, essentially freely through it, infrared light coming from source 36, and to reflect, and not pass through, light directed toward it from source 38. Light from these sources, when present, flows downstream along illumination path 50 (to the right in FIG. 1). As will be more fully explained below herein, and as was just mentioned above, light sources 36, 38 are operated independently and at different times, and accordingly, light from these two sources is not directed simultaneously along path 50. The alignments of these two light sources with respect to mirror 44 and to illumination path 50 is such that the elongate "ribbons" of light effectively projected from these sources downstream from mirror 44 along path 50 would perimetrally coincide with, and directly overlap, one another in a matching fashion were they to be projected simultaneously.

From dichroic mirror 44, light from sources 36, 38 flowing downstream in illumination path 50, and specifically in illumination path portion 50*a*, flows through lens 46, through the region occupied/occupiable by patterning reticle 48, to mirror 52 from which it is deflected angularly downwardly in FIG. 1 into illumination path portion 50*b*, thereafter through lens 54, then to the upwardly facing side (in FIG. 1) of beam splitter 56, from where one percentage-part of it is directed in and along angularly turned illumination path portion 50*c* toward pupil 24*c* in eye 24, and the other percentage-part of it passes through this beam splitter, on the other side of which it strikes, and is absorbed in and by, light trap 58.

Lenses 46, 54 have diameters herein of about 32-mm, and clear, circular apertures each of slightly lesser diameter. Lens 46 is disposed at its back focal plane distance from each of light sources 36, 38, and lens 54 lies at its back focal plane distance from pupil 24*c*. These two focal plane dimensions are the same. Lens 46 collimates light arriving at it from each of the light sources. Reticle 48, whose structure and operation will be described shortly, and below, is located at the front focal plane distance from lens 54.

Considering FIG. 4 along with FIGS. 1 and 2, beam splitter 56, which is located at the angular intersection of illumination path portions 50*b*, 50*c*, is angled in such a fashion that a ribbon of fundus-illumination light coming from one or the other of light sources 36, 38 is projected into the eye, through the pupil along the axis of path portion 50*c*, to illuminate the fundus by striking the eye as indicated generally at 57 in FIG. 4, and specifically, horizontally adjacent the lower portion of the pupil in the eye, such as the lower portion illustrated of pupil 24*c*. With an eye which is to be examined properly positioned relative to the optical componentry in system 10, a condition which is true, as mentioned earlier, for eye 24 herein, fundus-illumination light, derived from the ribbon of light just mentioned and illustrated in FIG. 4, will enter the eye just as is shown in FIG. 4, and will properly illuminate the fundus. This illumination condition regarding placement of the light-ribbon/eye "strike location" as pictured in FIG. 4, greatly minimizes the likelihood of optical interference occurring from light reflecting from the cornea, and additionally, allows for viewing and capture of fundus images along the axis of reflection-flow main branch 10B without there being any unwanted illumination-light content within the optical path of branch 10B. The earlier-mentioned, low disposition provided for the central axis of illumination-path portion 50*c* is responsible for this condition, and in FIG. 4, this path portion axis has its specific "strike location" at the site of the pupil appropriately there cross-marked as 50*c*.

Turning attention at this point to FIG. 5 in relation to FIG. 1, reticle 48 herein takes the form of a circular, light-occluding plate 48*a* having a diameter of about 32-mm, and including a predetermined, though not critical, pattern of plural, small (about 2-mm diameter), circular apertures, such as the apertures shown at 48*b*. Reticle 48 also includes a laterally extending arm 48*c* by way of which it is suitably mounted for reversible pivoting, or another form of reversible shifting, as indicated by double-headed arrow 49 in FIG. 1, between two different positions, or conditions, in one of which it is disposed substantially centrally across illumination path portion 50*a*, as it is so pictured in FIG. 1, and in the other of which it is swung completely out of the way so that it interrupts no illumination light flow in the illumination branch. When the reticle is in its first-mentioned condition, its effect is to cast a high-contrast-imagery shadow pattern, effectively matching the pattern of circular apertures in plate 48*a*, onto the fundus of an eye which is being examined. It does this, in accordance with preferred practice of the invention, for the purpose of creating high-contrast edge portions (at least one is needed) which play a role, as will be described shortly, in helping to establish precision focus of a fundus image on a camera sensor still to be described and discussed. Importantly in relation to achieving precision focus of a fundus image on the just-mentioned sensor, the contrast imagery formed by reticle 48 on the fundus of an eye is stable in space, in the significant sense that its spatial position is independent of eye movement.

Included in system 10 herein relative to reticle 48, but not shown specifically in the drawings, is a suitable motor structure which is operable for shifting the position/condition of the reticle as described. This motor structure is operated under the control of computer 14 through an appropriate control connection which is included in the earlier-mentioned collection of computer-associated connections represented schematically by bracket 14A.

Returning attention now principally to FIG. 1, reflection-flow main branch 10B possesses an optically central, elongate, main optical path 59 possessing a long, non-angular, central axis 59A. Path 59 extends from its upstream end which, as shown in FIG. 1 with system 10 in a correct operative condition relative to eye 24, is located at fundus 24*a*, to its downstream end which terminates at an electronic image sensor which is located within, and which forms a part of, a still-to-be-described, conventional digital camera located adjacent the left side of FIG. 1. It is path 59 which carries the mentioned fundus-reflection light derived from, and possessing a reflection image of the fundus. It is important to note, and this can be seen in FIGS. 1, 2 and 4, that path-59 axis 59A, where it "engages" pupil 24*c*, is spaced from and above the axis of path portion 50*c*. In FIG. 4, this axis "engagement" location is illustrated with a large dot. Path 59 throughout its length, in addition to carrying fundus-reflection light, as just mentioned, also carries light which acts as if the pupil in an eye, such as pupil 24*c* in eye 24, were its source.

Progressing in branch 10B in a downstream manner along path 59 from its upstream end toward its downstream end, branch 10B includes, optically sequentially, previously mentioned beam splitter 56, yet another circular-perimeter doublet lens 60, a beam splitter 62, still another circular-perimeter doublet lens 64 (the fourth one included in system 10), the device described earlier herein as a parallel plane shifter 66 (shown purposely angularly and isometrically), which is also referred to as discriminatory, light-content shifting structure operable selectively for producing relative trans-axial light displacement of non-collimated light striking its right, upstream side in FIG. 1, and a conventional, monochrome digital camera 68 which includes internal, multi-element lens structure 68a, a circular aperture 68b, and an electronic image sensor, or image-detecting sensor, such as a CCD sensor, 68c. Lenses 60, 64 are the same in size and optical characteristics as lenses 46, 54, and accordingly, all four of these lenses, as selected for use herein, have the same focal length. Camera 68 is the above-mentioned "still-to-be-described", conventional digital camera, and the downstream end of path 59 ends with sensor 68c. Looking at camera 68 along axis 59A, from the point of view of the right side of the camera in FIG. 1, aperture 68b appears herein from the outside of camera 68 to have a diameter of about 2-mm. Camera 68 may be thought of as being a fixed-geometry camera in the sense that no part of it moves, or needs to move, in relation to the manner in which it functions in system 10, and especially in relation to the matter of establishing precision focus of a fundus image on the camera's image sensor.

Particularly important to note about this "fixed-geometry" nature of camera 68 is the fact that, for capturing fundus images contained in reflection-flow branch 10B, the required, and relevant, "image-capture" aperture (68b) in the branch is stationary relative to the image-receiving sensor (68c) in the branch. This significant feature of the invention contributes to great simplification in the system of the invention in comparison with prior-art ocular fundus camera systems that employ spatially moving apertures at the functional location of aperture 68b.

Sensor 68c is suitably connected for image-data-transfer and image-display purposes to computer 14 via an appropriate data-flow connection which is among the computer-associated connections represented by bracket 14A.

System elements 64, 66, 68 within branch 10B are the several system optical elements, earlier discussed, that are mounted on previously mentioned, translationally adjustable subframe 26.

With illumination light flowing from one of sources 36, 38 in branch 10A along illumination path portion 50c toward eye 24, illumination light passing through the pupil in the eye, as just described above in relation to FIG. 4, falls on the fundus where it illuminates a region of the fundus whose shape is that of the clear aperture of lens 54—creating a disk of light on the fundus. Some light from this illuminated region of the fundus is reflected back through the pupil, essentially along the long axis 59A of optical path 59.

An appropriate part of this reflected light passes through beam splitter 56, through lens 60, through beam splitter 62, and through lens 64. Light which thus flows as reflection light along path 59 includes not only a reflection portion which carries an image of the illuminated fundus, but also, as mentioned earlier, a portion which acts as if pupil 24c were its source.

Lens 60 collimates that light portion in this flow which acts as though the pupil were its source—the pupil lying at the back focal plane of lens 60—and this collimated, "pupil" light portion then passes downstream to and through lens 64. Lens 64 effectively un-collimates the "pupil" light, and images it, and thus images the pupil, as non-collimated light through the parallel plane shifter, onto aperture 68b in camera 68. In the system now being described, the size of this projected image of the pupil will be larger than the opening of aperture 68b.

If we assume for current discussion purposes that eye 24 has no refractive error, meaning that an object located at an infinite distance from it will be in sharp focus on its fundus, the result of this condition will be that light reflected outwardly from each point on the fundus (the fundus-reflection light) will be collimated by the optics of the eye as this fundus-reflection light passes outwardly through the pupil. Under these circumstances, lens 60 will form, from this fundus-reflection light, an aerial image of the fundus at its front focal-plane distance which lies somewhere between lenses 60 and 64.

If we make the further assumption, for current discussion purposes, that lens 64 is disposed at its front focal-plane distance from the aerial image of the fundus just mentioned, lens 64 will collimate the reflection light from the fundus and direct it downstream through parallel plane shifter 66, toward and through aperture 68b in camera 68, and onto image sensor 68c on which the fundus image will be in proper focus. Aperture 68b lies at the back focal plane of lens 64.

Continuing within branch 10B, parallel plane shifter 66 is supported for motion relative to other components in system 10, and specifically is supported in a manner whereby it's plane, as mentioned earlier herein, is under all circumstances disposed at an angle of about 9-degrees, or inclined, relative to a plane that would lie normal with respect to axis 59A, and for rotation to different rotated positions on and about axis 59A. Because of this angularly mounted, and axial rotation, condition of the parallel plane shifter, also referred to herein as a plane-inclined shifter, rotational motion of it, as just described, if performed continuously about axis 59A, will cause the shifter to appear to wobble. In FIG. 1 in the drawings, the illustrated parallel plane shifter is shown in an orientation whereby a line (not illustrated) which is coincident with the shifter's axis of revolution and normal to its plane, lies in a plane (a) which contains axis 59A, (b) which is normal to the plane of FIG. 1, and (c) which has a "nearest-to-the-viewer" portion that extends toward the viewer relative to the plane of FIG. 1 and on the left side of the plane shifter in this figure.

Rotational motion of the parallel plane shifter is performed under the control of computer 14, and via a suitable, conventional drive motor (not shown) which is appropriately drivingly connected to this device. A control connection provided between computer 14 and this drive motor is among the connections represented by bracket 14A.

Specific operations involving rotation of the parallel plane shifter about axis 59A during practice of the methodology of the present invention will be described shortly. What is especially important to know, at least initially, about the optical behavior of the parallel plane shifter, in relation its rotated position on and about axis 59A, is that (a) this shifter functions under all circumstances, whether stationary or rotating, to produce what is, and has above been, referred to herein as trans-axial shifting, relative to axis 59A, and on its downstream side which faces aperture 68b in camera 68, of all non-collimated light striking it on its upstream side, which is the side that faces lens 64. This is a discriminatory operation which affects only non-collimated light. In other words, collimated light is not so shifted. What this means in system 10, under all operating circumstances, is that the image of the pupil in light which acts as if the pupil were its source, and which is downstream from lens 64, there in an un-collimated condition, and upstream from the parallel plane shifter, will always be imaged shiftably through the parallel plane shifter onto the plane of aperture 68b. The resulting image on sensor 68c, because of the presence of aperture 68b, will be formed only by light that exits the pupil of the eye through a circular region 2-mm in diameter It will be apparent from the discussion above regarding the optical behavior of the parallel plane shifter, that, with rotation of this plane-inclined shifter about axis 59A between any two, different rotated conditions, any image which is carried in non-collimated light that strikes the shifter's upstream side, such as the light which acts as if pupil 24c were its source, will be shifted movably laterally across aperture 68b, and will be seen through the aperture, within a 2-mm diameter presentation on sensor 68c, as an image positional shift by the sensor, whereas any image carried in collimated light striking the upstream side of the parallel plane shifter will not be shifted relative to aperture 68b, and will be seen by sensor through the aperture as a positionally stable 2-mm diameter image.

Recalling that reticle 48, when lying across illumination path portion 50a, is intended, through shadowing, to create, on an illuminated fundus, a plurality of high-contrast imagery edge portions, and that the reticle herein possesses circular apertures for accomplishing this task, which apertures, because of their circularity, will effectively produce "fundus-carrying" contrast edges that simultaneously lie in every possible two-dimensional direction as projected ultimately onto camera aperture 68b, if the reticle is so positioned to create this just described edge-contrast condition, then, under a circumstance with a non-collimated image of the shadow-patterned fundus striking the upstream side of the parallel plane shifter, if the plane shifter is rotated between any two, different rotated conditions about axis 59A, a high-contrast edge portion produced on the fundus by the reticle will clearly be seen by sensor 68b as a positionally shifted, moved image. As will be explained, the sharpness of this edge-contrast, shadow image on the fundus is not critical—merely its presence, and its content featuring at least one high-contrast edge which will lie at an angle to a direction of any trans-axial shift produced by the parallel plane shifter as just described. It is this detectable, contrast-edge-shift phenomenon, as will be discussed below, which forms the basis for achieving, inter alia, precision, reticle-assisted focusing of a fundus image on sensor 68c.

Turning attention at this point specifically to FIG. 4, illustrated therein, within the large circle which represents pupil 24c, are three, small circles, two of which are shown in dashed lines at 78, 80, and the third of which is shown in a dash-double-dot line at 82. Circles 78, 80 lie vertically centered adjacent one another on a horizontal, dash-dot line 84, tangent to each other and to the marked large dot which indicates the point where axis 59A "engages" the pupil. Circle 82, which is also tangent to the dot that is marked 59A, is disposed slightly upwardly and to the right of this dot, centered along another dash-dot line 86 which passes through the dot, and which extends at an acute angle α relative to line 84.

These three circles, or circular areas, represent three, different-position portions of reflection light coming from the fundus and passing through the pupil, along path axis 59A, and through lens 60, beam splitter 62, lens 64 and parallel plane shifter 66, which will be imaged onto sensor 68c depending upon the position of the parallel plane shifter on and about axis 59A. With the parallel plane shifter in different rotated conditions/positions relative to axis 59A, the structure of system 10 is organized and sized in such a fashion that all such "drawing-representable" circular areas which, as just explained, represent fundus-imagery content that will be projected through the parallel plane shifter and aperture 68b onto sensor 68c will lie tangent to the dot represented in FIG. 4 at 59A, and at different angular locations around that dot depending upon parallel plane shifter position. The "composite" (larger circular) area of the fundus which is defined by the overlapping locations of these "fundus-image-reflection" circles lies spaced above the ribbon of incoming illumination light, and thus, very importantly as mentioned earlier herein, the light forming the outcoming fundus image of reflection-interest always passes through a different region of the pupil than the region through which the illumination light passes.

Reinforcing at this point certain light-shifting descriptive information just given above, with respect to shifting of non-collimated light by the parallel plane shifter, it will always be the case that the entire image of the pupil will be shifted by this parallel plane shifter across aperture 68b, and, depending upon the shifted position of the image of the pupil, sensor 68c will see an image of the entire illuminated fundus drawn from a small circular region of the entire area of the pupil image at the location of the plane of aperture 68b, such as areas represented by circles 78, 80, 82 in FIG. 4.

With parallel plane shifter 66 in the rotated condition illustrated for it in FIG. 1, the small circular region of the pupil image which will be presented to aperture 68b, and therethrough to sensor 68c, is that region of the pupil image which is represented by the small circle designated 78 in FIG. 4. In a precision-focusing procedure, which will very shortly be described in detail, the parallel plane shifter is rotated on and about axis 59A 180-degrees from the condition in which it is pictured in FIG. 1, and under this circumstance, the area of the pupil image which will be presented to aperture 68b, and therethrough to sensor 68c, will be that region of the pupil image which is represented by the small circle in FIG. 4 designated 80. Under all other rotated conditions of the parallel plane shifter, other small circular regions of the pupil image, such as the region represented by small circle designated 82 in FIG. 4, will be presented directly to aperture 68b for projection onto sensor 68c.

Completing now a description of the structure of system 10, system positioning branch 10C includes a pair of conventional, monochrome digital cameras 70, 72, a pair of lenses 74, 76 that are associated, respectively, with cameras 70, 72, previously mentioned beam splitter 62, previously mentioned lens 60, and previously mentioned beam splitter 56. As is intended to be indicated by the "vertical" fragmentation lines which, in FIG. 1, form "divisions" between designated cameras 70, 72 and between designated lenses 74, 76, camera 70 and its associated lens 74 are to be understood as lying above the plane of FIG. 1, i.e., toward the viewer relative to the plane of FIG. 1, and camera 72 and its associated lens 76 as lying below the plane of the figure, i.e., away from the viewer relative to the plane of FIG. 1. Cameras 70, 72 include electronic image sensors (not illustrated) which are suitably connected for image-data-transfer and image-display purposes to computer 14 via appropriate, respective data-flow connections which are also among the computer-associated connections represented by bracket 14A.

These parts in branch 10C in system 10, and how they function in the operation of the system, will also be more fully talked about shortly.

In much of the description which has been given so far regarding, ultimately, (a) the character of "image-from-the-fundus" light flow in the reflection-flow branch in system 10, and (b) the matter of how input fundus illumination takes place in order to create such fundus-reflection imagery flow, certain initial, and descriptively useful, simplifying assumptions have been made. As a reminder, one of these assumptions has been that all of the optical components on frame 12 in the system have been, preliminarily, positioned correctly, in an overall systemic sense, with respect to an eye, such as eye 24, whose fundus is to be examined. Another assumption has been that the particular eye involved has associated with it no refractive error. A third assumption has been that the mentioned aerial image of the fundus which is created by lens 60 between lenses 60 and 64 lies both at the front focal plane of lens 60, and also at the front focal plane of lens 64.

With all of these assumptions in place, an idealized situation exists, whereby an image of fundus 24*a* will be, as mentioned above, in proper focus on sensor 68*c*.

However, and now moving beyond these initially convenient assumptions, we will here set these assumptions aside, and discuss, from a systemic-operational and methodologic point of view, the issues of overall, proper, relative positioning between system 10 and an eye, and of fundus-image focusing under circumstances with such positioning established, and do these things recognizing that a system setup and operation always requires recognition that the presence of eye refractive error is a non-controllable, potential given for each eye whose fundus is to be examined.

As pointed out, before system 10 can be used for fundus examination, it is critical that, initially, the system as a whole be properly positioned and aligned with respect to the subject eye. The procedure for accomplishing this, which occurs under the combined control of computer 14 and a system operator, is now described with the recognition that positional adjustments of the system componentry as a whole will take place through maneuvering, relative to an eye which is to be examined, the translational, angular, and rotational dispositions in space of frame 12. The several, system-aligning steps that are now set forth in this description are basically conventional in nature, and will be well understood by those skilled in the relevant art without much step elaboration.

A subject whose fundus is to be examined is seated in what might be thought of as an examination station, and is asked to direct the gaze of his or her eye-to-be-examined through a conventional viewing instrument (not illustrated herein) provided at that station, and to focus that eye's attention on a small flashing light, such as a small blue light, which is visible in the field of view provided by this instrument.

The front of the eye, with a subject appropriately so seated and positioned relative to the mentioned viewing instrument, is illuminated by an infrared LED (not light source 36, and not specifically shown in the drawings herein) which is simply aimed at the eye. Additionally, light source 36 is turned on, and light source 38 is left off.

Light reflected from the region of the front of the eye, and light reflected from the fundus, passes through beam splitter 56 and lens 60 toward beam splitter 62. A small percentage of this light which strikes beam splitter 62 is reflected downwardly toward laterally spaced lenses 74, 76 and their respectively associated, laterally spaced cameras 70, 72. It will be remembered at this point that lens 74 and camera 70 lie toward the viewer of FIG. 1 relative to the plane of FIG. 1, whereas lens 76 and its associated camera 72 are disposed away from the viewer of FIG. 1 relative to the plane of FIG. 1. Lenses 74, 76 herein possess considerably smaller diameters than does lens 60.

Under these circumstances, lens 74 and camera 70 catch light passing through a circular region which is disposed effectively on one side of lens 60, and lens 76 and camera 72 catch light passing through a circular region which is disposed effectively on the other side of lens 60. These just-mentioned sides of lens 60 are, of course, related to the locations of lenses 74, 76 and cameras 70, 72 relative to the opposite sides of the plane of FIG. 1. With this condition in place, each of cameras 70, 72 is positioned to provide a respective view of the pupil, one through the left side of lens 60, and the other through the right side this lens.

The image of the pupil acquired by camera 70 is displayed on a conventional display screen (not shown) suitably connected to computer 14, and the system operator uses an appropriate cursor-moving device, such as a mouse, to instruct the computer to drive frame 12 so as approximately to center the image of the pupil in a window presented on this screen. When the pupil is approximately centered in this window, infrared light from source 36 will enter the pupil and illuminate the fundus. Based upon such illumination, light then reflected outwardly from the fundus will back-illuminate the pupil, making it appear bright in the pupil image on the screen.

In the operation, at this point in the aligning process, of system 10, and triggering, and then based upon, suitable (and conventional) algorithmic programming resident in computer 14, the system operator will, as by a "mouse-button click", instruct the computer to finish the alignment task through initiating, and carrying through to a condition of alignment completion, a series of appropriate computer-implemented movement iterations of frame 12 to produce perfect registration of the images acquired by cameras 70, 72, as well as centering of these images relative to a defined point for centering. With such registration and centering accomplished, system 10 is then properly positioned relative to the eye which is about to have its fundus examined.

With system-eye alignment completed, attention necessarily turns to focusing of the fundus image on sensor 68*c*, and preparing the sensor-received image for examination. This will often, if not usually, need to be done, in terms of basic proper focusing, in order to deal with refractive error in the eye whose fundus is to be imaged.

We describe herein two manners of achieving such focus, the first and preferred one of which involves the use of reticle 48, and the second one of which involves simply using iterative views of the fundus image itself and computer performed Fourier spatial-frequency-content analyses of these views. The second approach is usable principally in a modified form of the invention which does not include a patterned reticle.

With basic fundus-image focus achieved, sensor-received-image preparation—as, for example the performance of plural captured images registration—for fundus-image study and examination purposes, is controlled strictly in the computer electronics environment under software control.

Beginning with a description of the preferred manner of focusing, if the eye is either nearsighted or farsighted, i.e., characterized with a refractive error, then the aerial image of the fundus produced by lens 60 will almost certainly not initially, that is right after the establishment of proper system-eye alignment, be located at the front focal plane distance of and from lens 64, as discussed earlier herein, and, without the making of an appropriate translational positioning adjustment in focusing assembly 26, the image of the focus formed on image sensor 68c will not be in focus.

To establish precision focus, infrared light source 36 is turned on, green light source 38 is off, reticle 48 is shifted into the illumination path in path portion 50a therein to create a high-contrast shadow-pattern image on the fundus, and the parallel plane shifter 66 is placed in the position shown for it, and described in relation to this showing, in FIG. 1—a position such that the image of the pupil is shifted horizontally toward the viewer in FIG. 1 relative to the plane of this figure. Under these conditions, an image of the shadow of the reticle is, as mentioned, formed on the fundus by lens 54 and the optics of the eye, and an image of the image of the fundus is formed on image sensor 68c.

This image, which we will call "Image 1", is saved.

The parallel plane shifter is then rotated 180 degrees to change it position, and so that the image of the pupil becomes shifted away from the viewer in FIG. 1 relative to the plane of this figure, and another image of the image of the fundus is then formed on sensor 68c.

This next image, which we will call "Image 2", is saved.

Such changing of the rotated condition of the parallel plane shifter between these two 180-degree positions will, in an "out-of-focus" condition of the fundus image, cause the contrast edges, or contract edge portions, in the reticle-created, fundus-reflected shadow image to shift very noticeably in the image received by sensor 68c. The direction in which such a contrast-edge shift occurs, and the amount of shift which takes place, will provide computer 14 with initial focus-adjusting corrective information to be supplied appropriately for controlling motor structure 30 so as to move subframe 26, and thus lens 64 and the other optical elements carried on this subframe, effectively closer or farther away from lens 60 in a manner striving toward a condition of accurate focus—a condition which will exist when the aerial image of the fundus created by lens 60 resides at the front focal plane distance from lens 64, whereby the image of the fundus will be collimated by lens 64 as it flows from lens 64 toward the parallel plane shifter.

In this now computer-active process, and in accordance with the computer's programming (which is conventional in nature as mentioned earlier herein), computer 14, electronically and internally, shifts saved Image 1 with respect to saved Image 2 until these two images are superimposed or registered. This software-implemented internal, electronic shifting is directly effective to create an appropriate positioning control signal which is delivered by the computer to motor structure 30 to produce mechanical position-shifting of the focusing assembly so as to locate the aerial image of the fundus precisely at the front focal plane distances of each of lenses 60 and 64. This activity is done in final preparation for study of an in-focus, sensor-received fundus image.

This entire reticle-based focusing and image preparation process just described is iterated, if necessary, until completed successfully to within appropriate, predetermined tolerances.

In practicing the modified-system, non-reticle focusing process mentioned above, a process which is based upon employing natural image-contract characteristics of an image-sensor-received fundus image, per se, special attention, and dealing, must be paid to the fact that the human eye is in constant motion. A way of thinking about this practice is that it relies, for achieving precision fundus-image focus, upon acquiring and using information regarding the perceived "goodness of such focus" itself as the guide for adjusting and achieving desired focus. Complicating matters in this focusing approach is that unless the source of light employed to illuminate the fundus is extremely bright, normal eye motion will cause sensor-perceived blurring of fundus features, which motion-caused blurring is difficult to distinguish from blurring caused by poor focus.

Here in this practice, to achieve good focus, a series of images is collected at a series of different positions of the system focusing assembly, each image is subjected to computer-implemented Fourier analysis, and the one in best focus is selected by choosing the image with the greatest high spatial frequency content, notwithstanding unavoidable blurring due to eye motion.

Once system alignment and fundus-image focusing have been accomplished, system 10 is ready for a fundus-imaging process.

Under computer control, and with respect to a condition with infrared light source 36 turned on and light source 38 turned off, the image of the fundus received by the sensor 68c is analyzed in order to determine an optimal exposure duration value, and this value is then set for the next series of events. The parallel plane shifter is, first, positioned as it is illustrated in FIG. 1, and a series of images, containing a number of images determined by the system operator, is taken with the images captured and stored. The parallel plane shifter is then adjusted to what has been described above as its 180-degree position, and another similar series of images of the fundus resident on sensor 68c is captured and stored.

With these two series, or sets, of images thus acquired, one set of which has been taken effectively with light passing through one side of the pupil, as through the small circular region designated 78 in FIG. 4, and the other set of which has been taken with light passing through the other side of the pupil, as through the small circular region designated 80 in FIG. 4, a computer-implemented, conventional image-registration and averaging procedure for each set—averaging being performed in order to improve signal-to-noise ratio in the images—takes place. What then exists in available computer-14 storage is, effectively, a stereo pair of focused images of the relevant fundus.

Next to occur is that the infrared light source, 36, is turned off, the green light source, 38, is turned on, and the entire, now-completed, red-light-illumination imaging process which has just been described, beginning with proper exposure determination, and the acquiring of plural sets of images with the parallel plane shifter in each one of its two, described, 180-degree positions, is performed under conditions of green-light fundus illumination.

What are then available for suitable, user-determined study and examination, under appropriate computer-14 control, are both individual, well focused red-illumination and green-illumination fundus images, and, if desired, what is known as a sequential-color stereo image of the fundus which is easily computer renderable.

Regarding now the matter of eye refraction, and the acquisition of data relevant to its correction, and in relation to practice of the present invention to accomplish the gathering of relevant refractive-error eye data leading to what is called autorefraction, when eye care specialists perform what they call a "refraction"—a the process of determining a prescription for refractive-error vision correction—the related, "refraction" vision examination typically results in the obtaining of three parameter numbers, known by traditional names as "Sphere", which is the optical power of a lens component required for the correction consisting purely of a spherical surface, "Cylinder", which is the required power of a lens component consisting entirely of a cylindrical surface, and "Axis", which is the angle, in the sense of wheel rotation about the patient's line of sight, of the cylindrical component. (Some examinations and resulting prescriptions also include a term called "Prism", but the process of autorefraction, as it is always performed according to prior-art practices, and as it is performed in accordance with the present invention, does not measure "Prism".) These three (or four) components are combined in each spectacle lens or contact lens, for example by grinding the required cylindrical surface into the front of the lens and the spherical surface into the back of the lens.

To perform autorefraction in the practice of the present invention, reticle 48 is inserted into the optical illumination path, the infrared LED, 36, is turned on and the green LED, 38, is left off, and the fundus focusing assembly, 26, is set in the position for best focus of the fundus image if the eye were to have zero refractive error.

A small light that appears to the subject to be straight ahead, that is, centered on lens 60, is turned on and the patient is asked to look at it.

Parallel plane shifter 66 is then rotated about axis 59A into each in a series of different angular positions (currently, separated by sixteen equal angles), and an image of the shadow pattern created by reticle 48 on the fundus, passing through the pupil at respective, different locations thereof, is collected in each of these positions. One of such "different" angular positions, in terms of the passage of fundus-reflection light through the pupil, other than the two, above-described, "180-degree angular positions" that have been identified in relation to the small circular regions 78, 80 in FIG. 4, and discussed in relation to fundus-image focusing, which two regions' reflection light flows are included in this collection of images, is represented in FIG. 4 by small circular region 82.

In software then, all of these images are registered, and the horizontal and vertical shifts required for registration are saved. Also in software, the "x, y" shifts required to register each image is (virtually) plotted as a point in two-dimensional space, with the plot origin being x=0, y=0. These points, in a set, will lie approximately on an ellipse, centered on the origin, and in software, the ellipse that best fits this set of points is computed.

The result is displayed as follows: the short axis of the ellipse (multiplied by a calibration factor) is defined as the "Sphere"; the long axis of the ellipse minus the short axis (times the calibration factor) is defined as the "Cylinder"; and the angle of the long axis of the ellipse is the "Angle".

In an alternative data-specification convention, the short axis of the ellipse is defined as the "Sphere", the short axis minus the long axis is defined as the "Cylinder", and the angle which is disposed at 90 degrees from the long axis of the ellipse is defined as the "Angle".

Accordingly, a preferred and best-mode embodiment of, and a manner of practicing to accomplish certain tasks regarding, the present invention have been described and illustrated. Having said this, we fully recognize that variations and modifications, some of which we have suggested herein, may well come to the minds of those generally skilled in the relevant art, and it is our intention that all such variations and modifications will be treated as coming within the scopes of the following claims to invention.

We claim:

1. An ocular fundus camera system comprising:
   light-source for illuminating, along an elongate, illumination path, the fundus in a subject's eye,
   an optical path having upstream and downstream ends and a long axis, extending downstream from the subject's eye, and carrying, downstream along its length, both light that acts as if the pupil were its source, and light reflected from, and carrying an image of, the fundus,
   an image-detecting sensor disposed for optical communication with light carried in said path,
   an aperture on the path's long axis, operatively associated with, and stationary with respect to, said sensor at a location which is upstream along the path from the sensor, positioned there to communicate to the sensor light carried in the path,
   a discriminatory, light-content shifting structure disposed centrally on said path's long axis upstream therealong relative to said aperture, operable selectively for producing, within that portion of the main path which is disposed intermediate the shifting structure and the aperture, relative trans-axial displacement-shifting solely of any non-collimated light carried in that portion of the path which is disposed upstream from the shifting structure, and
   a structure selectively placeable across said illumination path for introducing, effectively, into light reflected from the fundus, edge-portion-containing optical contrast imagery having at least one, contrast edge portion which lies at an angle relative to the direction of trans-axial shifting producible by said shifting structure, and whose spatial disposition in the fundus-reflection light is independent of eye movement.

2. The system of claim 1, wherein said structure is a circular, light-occluding plate that forms a shadow patterning reticle.

3. The system of claim 1, wherein said at least one contrast edge portion is a pattern of plural circular apertures.

4. An ocular fundus camera system usable in relation to a light-illuminated fundus in a subject's eye, and including an elongate, main optical path having upstream and downstream ends and a long axis, and which main path extends downstream from a person's eye and carries both (a) light that acts as if the pupil were its source and (b) light reflected from, and carrying an image of, the fundus, said system comprising
   an image-detecting sensor disposed along said main path adjacent the main path's downstream end, and in optical communication with light carried in said path,
   an aperture on the main path's long axis, operatively associated with, and stationary with respect to, said sensor at a location which is upstream from the sensor, and
   an optical, light-content shifting structure, operable selectively for producing, within that portion of the main path which is disposed downstream from the shifting structure, relative trans-axial displacement solely of any non-collimated light carried in that portion of the main path which is disposed upstream from the shifting structure.

5. The system of claim 4, wherein (a) said sensor is an electronic device, (b) the system includes a digital computer which is operatively connected to selected system elements including the sensor from which it is adapted to receive imagery detected by the sensor, (c) any relative trans-axial displacement produced by said light-shifting structure is detected by the sensor and through the sensor also by said computer, and (d) said computer is structured to respond to any such light-shift detection in a manner designed to minimize the presence of non-collimated light carried in that portion of the main path which is disposed upstream from the shifting structure.

6. The system of claim 5, wherein said computer is provided with appropriate operative connections to elements in said system whereby a computer response which is operative to minimize the presence of non-collimated light carried in that portion of the main path which is disposed upstream from the shifting structure is a response tending better to focus an image of the fundus on said sensor.

7. The system of claim 4, wherein said light-content shifting structure takes the form of a parallel plane shifter.

8. The system of claim 4 which further comprises structure for introducing, into light reflected from the fundus, edge-containing optical contrast imagery having at least one contrast edge portion which lies at an angle to the direction of trans-axial shifting producible by said shifting structure.

9. The system of claim 4 which further comprises light-source structure operable and arranged to illuminate the fundus substantially along an elongate optical illumination path which is independent of said main path, and to do so in a manner avoiding related illumination reflections along the main path from the cornea.

10. The system of claim 4, wherein said light-source structure includes independently energizable red and green light sources.

11. A method comprising:
   illuminating the fundus in a subject's eye along an elongate illumination path,
   creating, by said illuminating, a light reflection from the fundus directed therefrom outwardly through the pupil in a flow of reflection light which progresses downstream from the eye along an elongate main optical path having a long axis,
   discriminatorily, and in a relative trans-axial displacement manner at a location along the main optical path which is disposed downstream from the eye, shifting solely any non-collimated light which is contained in the flow of created reflection light,
   detecting any such shifting, and
   employing any detected shifting in a manner designed to minimize the presence of non-collimated light in the reflection-light flow.

12. The method of claim 11, wherein said shifting is performed by selected rotation, on the long axis of the main optical path, of a rotatable parallel plane shifter placed at the mentioned main optical path location in a condition with its plane disposed at an angle to the main optical path's long axis.

13. The method of claim 11 which further comprises, in a manner non-movably centered on the main optical path's long axis, at a second location along that axis which is disposed downstream from the first-mentioned, main optical-path location, aperturing a portion of the flow of reflection light, and wherein said detecting involves, at yet another location along the main optical path's long axis, which other location is disposed downstream from where aperturing takes place, electronically sensing the apertured light-flow portion, and said employing to minimize non-collimated light presence in the reflection light flow involves using an outcome of said electronic sensing.

14. The method of claim 13, wherein minimization of non-collimated light presence in the reflection light flow effects focusing of the apertured light flow at the location where sensing occurs so as to obtain a focused image of the illuminated fundus.

15. The method of claim 12, wherein said plane is disposed at an angle to a plane that is normal to the main optical path's long axis.

\* \* \* \* \*